(12) United States Patent
Lund et al.

(10) Patent No.: US 8,192,411 B2
(45) Date of Patent: Jun. 5, 2012

(54) DISPOSABLE OSTOMY IRRIGATION SLEEVE

(75) Inventors: Lars Lund, Vejle (DK); Henning Hedegaard, Sunds (DK)

(73) Assignee: GP Medical Devices ApS, Sunds (DK)

( * ) Notice: Subject to any disclaimer, the term of this patent is extended or adjusted under 35 U.S.C. 154(b) by 824 days.

(21) Appl. No.: 12/086,236

(22) PCT Filed: Jul. 7, 2006

(86) PCT No.: PCT/DK2006/000400
§ 371 (c)(1),
(2), (4) Date: Jun. 25, 2008

(87) PCT Pub. No.: WO2007/065429
PCT Pub. Date: Jun. 14, 2007

(65) Prior Publication Data
US 2008/0306460 A1 Dec. 11, 2008

(30) Foreign Application Priority Data
Dec. 8, 2005 (DK) .................................. 2005 01737

(51) Int. Cl.
*A61F 5/44* (2006.01)
*A61G 9/00* (2006.01)
*B60R 15/00* (2006.01)

(52) U.S. Cl. ................. 604/334; 4/114.1; 4/451; 4/452; 4/454; 4/455; 4/460

(58) Field of Classification Search .................. 604/334; 4/114.1, 451, 452, 454, 455, 460
See application file for complete search history.

(56) References Cited

U.S. PATENT DOCUMENTS

| | | | | | |
|---|---|---|---|---|---|
| 2,855,607 | A | * | 10/1958 | Sullivan | 4/144.2 |
| 2,869,547 | A | * | 1/1959 | Yohe | 604/334 |
| 3,200,415 | A | * | 8/1965 | Breece, Jr. | 4/144.2 |
| 3,591,870 | A | * | 7/1971 | Friesen et al. | 4/144.2 |
| 3,597,770 | A | * | 8/1971 | Jacuzzi et al. | 4/144.2 |
| 3,654,064 | A | * | 4/1972 | Laumann et al. | 428/191 |
| 3,672,370 | A | * | 6/1972 | Marsan | 604/277 |
| 3,763,502 | A | * | 10/1973 | Laumann | 4/452 |
| 3,825,005 | A | * | 7/1974 | Fenton | 604/335 |
| 3,830,235 | A | * | 8/1974 | Marsan | 604/277 |
| 4,023,216 | A | * | 5/1977 | Li | 4/144.3 |
| 4,296,502 | A | * | 10/1981 | Bortle | 4/144.1 |
| 4,586,927 | A | * | 5/1986 | Jensen | 604/342 |
| 4,734,941 | A | * | 4/1988 | DeWitt et al. | 4/144.4 |
| 4,755,421 | A | * | 7/1988 | Manning et al. | 442/338 |
| 4,762,738 | A | * | 8/1988 | Keyes et al. | 428/34.3 |
| 4,937,890 | A | * | 7/1990 | Tafur | 4/144.4 |

(Continued)

FOREIGN PATENT DOCUMENTS

EP 628278 12/1994

(Continued)

*Primary Examiner* — Tatyana Zalukaeva
*Assistant Examiner* — Ginger T Chapman
(74) *Attorney, Agent, or Firm* — James Creighton Wray

(57) ABSTRACT

Ostomy irrigation sleeve having a tubular shape and a first end with a first opening for receiving ostomy discharge material and a second, opposite end with a second opening for discharge of the ostomy discharge material into a discharge unit, for example a toilet, after guidance through the sleeve. The irrigation sleeve is made of a flexible, water soluble material configured to be water soluble only after a certain time of exposure to liquid, wherein the certain time is at least 3 minutes.

16 Claims, 5 Drawing Sheets

U.S. PATENT DOCUMENTS

Figure 1:
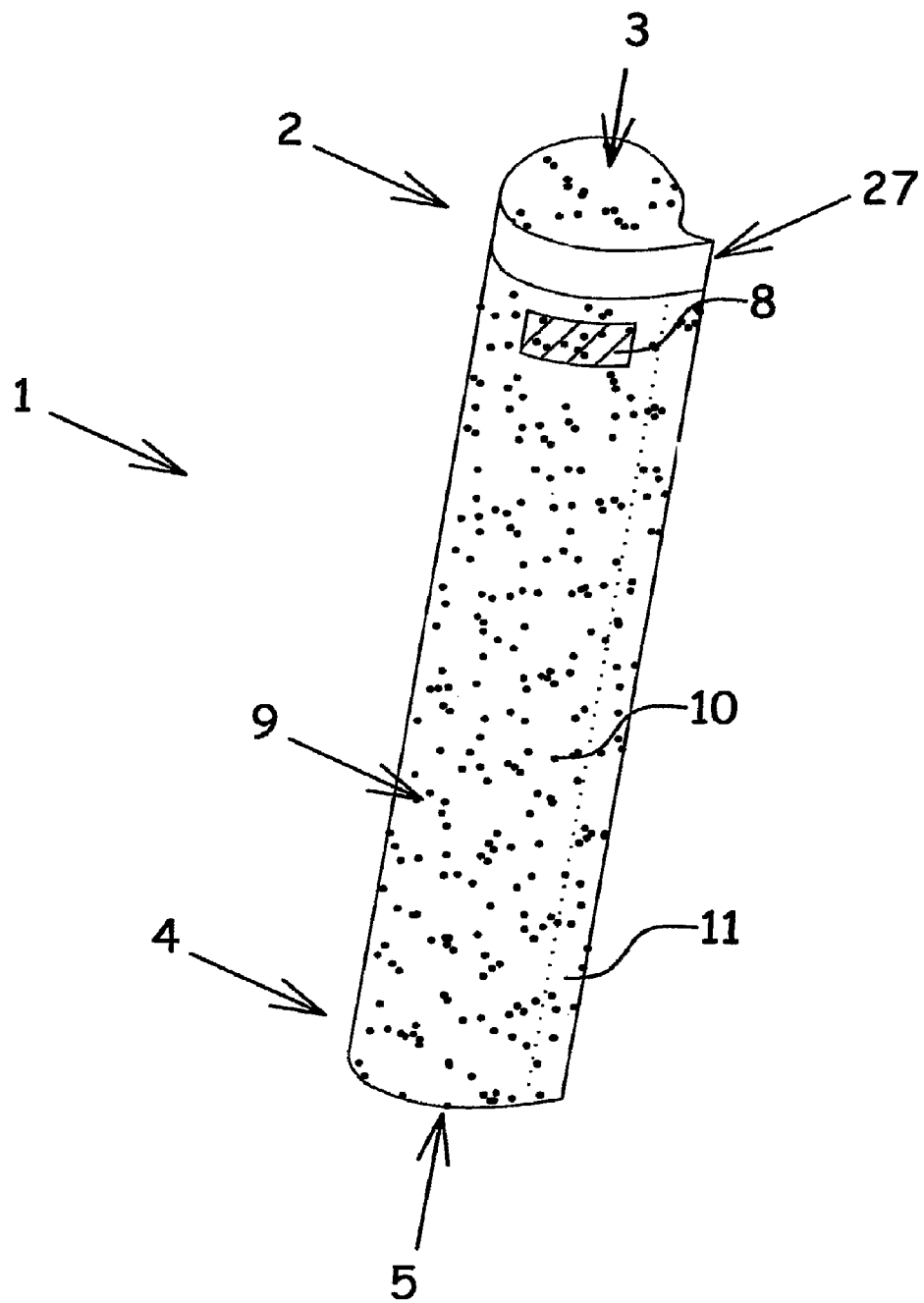

| | | | | |
|---|---|---|---|---|
| 5,067,821 A | * | 11/1991 | Young | 383/36 |
| 5,662,630 A | * | 9/1997 | Raynie | 604/349 |
| 5,722,136 A | | 3/1998 | Jonec | |
| 5,948,399 A | * | 9/1999 | McGlothlin | 424/76.1 |
| 6,199,220 B1 | * | 3/2001 | Smith | 4/144.2 |
| 6,324,704 B1 | * | 12/2001 | Imo | 4/144.2 |
| 6,345,911 B1 | * | 2/2002 | Young et al. | 383/6 |
| 6,460,200 B1 | * | 10/2002 | Mottale et al. | 4/144.4 |
| 6,495,080 B1 | * | 12/2002 | Tsai et al. | 264/143 |
| 6,620,142 B1 | * | 9/2003 | Fluckiger | 604/349 |
| 6,783,826 B2 | * | 8/2004 | Sherrod et al. | 428/35.7 |
| 7,241,711 B2 | * | 7/2007 | Takai et al. | 442/414 |
| 7,250,382 B2 | * | 7/2007 | Takai et al. | 442/414 |
| 2006/0090250 A1 | * | 5/2006 | Bolles | 4/144.2 |
| 2008/0262446 A1 | * | 10/2008 | Ryder et al. | 604/317 |
| 2009/0077734 A1 | * | 3/2009 | Ledo | 4/484 |
| 2010/0152686 A1 | * | 6/2010 | Ryder et al. | 604/332 |

FOREIGN PATENT DOCUMENTS

| | | |
|---|---|---|
| WO | WO 96/04872 | 2/1996 |
| WO | WO 2004/004613 | 1/2004 |

* cited by examiner

DISPOSABLE OSTOMY IRRIGATION SLEEVE

This application claims the benefit of Danish Application No. PA 2005 01737 filed Dec. 8, 2005 and PCT/DK2006/000400 filed Jul. 7, 2006, which are hereby incorporated by reference in their entirety.

FIELD OF THE INVENTION

The present invention relates to an ostomy irrigation sleeve.

BACKGROUND OF THE INVENTION

In order for re-usable ostomy (colostomy, ileostomy, urostomy) containers to be emptied into the toilet, it is customary to use irrigation sleeves of which one open end is positioned in the toilet, whereas the other end is placed under the ostomy pouch in order to receive the body excretions for disposal from the ostomy pouch.

Ostomy sleeves according to prior art, such as produced by the Danish company Coloplast, are made of plastic material in order to be water resistant and to withstand the pressure that may occur inside the sleeve during discharge of the excretions. In addition, the sleeves are re-usable. However, the re-use requires that the sleeves after use are cleaned at least to a certain extend. This cleaning is not very user-friendly and disliked because of the smell from the excretions, why a solution to this problem is desired.

DESCRIPTION

Summary of the Invention

It is the purpose of the invention to provide an ostomy sleeve that does not have the aforementioned disadvantages. This purpose is achieved with a disposable ostomy sleeve having a tubular shape and a first end with a first opening for receiving ostomy discharge material and a second, opposite end with a second opening for discharge of the ostomy discharge material into a discharge unit, for example a toilet, after guidance through the sleeve, wherein the irrigation sleeve is made of a flexible, water semi resistant material configured to be water soluble only after a certain time of exposure to liquid, wherein the certain time is at least 3 minutes.

A disposable ostomy sleeve, for example a colostomy sleeve, entirely made of water semi resistant material can be discharged into the toilet together with the remaining excretions in the sleeve. Semi resistant in this connection has to be understood that the material is resistant to exposure to water for a certain time.

This allows the user/patient to escape the unattractive cleaning of the sleeve. As has turned out, the discharge of the excretions through the sleeve can be done quickly by the user, such that a water resistance of the sleeve is only required for a minimum time, such as at least 3 minutes. However, in certain situations, the minimum time length may be at least 5 minutes giving also older users appropriate time.

The material to be used can, for instance, be the same type of paper material, as it is known for use as disposable toilet seat covers in public restrooms.

In a special embodiment, the discharge tube is made of a material which is in accord with the ISO 5263 standard. This implies when the material is discharged through the toilet into the sewage system, it attains a 99.8% degree of defibrillation within 30 minutes during normal circulation in a temperature decrease from 38° C. to 5° C.

In a further embodiment, the discharge tube is provided with a perforation along the sleeve. The perforation allows escape of air from inside the sleeve and through the perforation, which is important in order to allow the sleeve to sink properly in the water of the toilet and to ensure an easy flushing out of the toilet. In this connection, it is advantageous, if the entire tube contains a perforation.

In a practical embodiment, the perforation comprises holes in the sleeve with a diameter of less 1 mm in order to prevent discharge material to flow through the perforation. For example, the holes may have a diameter of less than 0.5 mm, such as 0.3 or 0.2 mm or even 0.1 mm. The number of holes may vary dependent on the size of the holes. For example, the density of holes may be 1-10 per $cm^2$.

In order to achieve a high strength in the longitudinal direction, the material of the sleeve may contain fibres that are oriented primarily in the longitudinal direction of the sleeve. For example, the sleeve may be made of paper with long cellulose fibres oriented primarily along the sleeve.

Normally, paper rolls for manufacture of paper articles have this kind of fibres arranged in the longitudinal direction. The manufacture of ostomy sleeves from these paper rolls can be achieved in an easy way by bending the paper around a longitudinal cylinder during roll off from the paper roll and after the bending, gluing the sides of the paper from the paper roll together in the longitudinal direction in order to form the sleeve. In order to ensure complete dissolution in water, also the glue should be water soluble.

In a further embodiment, the sleeve is primarily made of a laminate of at least two sheets of fibre material, where each of the at least two sheets contains fibres that are oriented primarily in a certain direction, where the at least two sheets are arranged in the laminate with different fibre directions. For example, the fibre directions for each sheet may be at 45 degrees relative to the longitudinal direction of the sleeve. Alternatively, the primary fibre direction for the first sheet may be in the longitudinal direction of the sleeve, whereas the primary fibre direction of the second sleeve is at right angles thereto. In a further alternative embodiment, the primary directions of the fibres for each sheet may be at an angle of less than 45 degrees with respect to the longitudinal direction of the sleeve, for example at 30 degrees.

In a practical embodiment, the irrigation sleeve according to the invention is made of paper with a weight of between 15 and 50 grams per square meter—endpoints included—preferably around 22 grams per square meter. Optionally, the sleeve is made of paper which is machine glazed on one side, namely the inner side of the sleeve, in order to achieve a smooth inner surface.

Experiments have shown a proper functioning of sleeves made of paper that in a dry state has longitudinal pull strength of at least 1, preferably around 1.6, according to the SCAN P-67 standard. In addition, experiments have shown a proper functioning, if the sleeve is made of paper that in a dry state has longitudinal tear strength of at least 100, preferably around 115, according to the ISO 1974 standard.

For the corresponding transverse properties, experiments have proven sufficiency for a transverse pull strength of at least 0.5, for example around 0.7, according to the SCAN P-67 standard. The transverse tear strength may be at least 150, for example 175 according to the ISO 1974 standard.

The irrigation sleeve according to the invention may be provided with an upper area with glue to be fastened to the ostomy pouch, for example colostomy pouch, during emptying of the pouch. In order to provide means for securely holding the sleeve, the sleeve may be equipped with a handle at the upper end. Such a handle may be glued to the remaining part of the sleeve. The uppermost part of the sleeve may be enforced by an enforcement ring around the upper edge of the sleeve. In order for the handle to be made as stable as possible, the reinforcement ring may have lips that extend a distance up along the handle.

A sleeve according to the invention may have a typical length between 0.5 m and 1 m, for example in the order of 0.6 m. It may have a diameter between 8 and 15 cm, for example in the order of 10 cm in the case of a cylindrical sleeve. A certain embodiment comprises a conical sleeve with an upper diameter in the order of between 10 cm and 12 cm and a lower diameter in the opposite end in the order of 8 cm.

The preferred material for a sleeve according to the invention is water semi resistant paper. However, other water soluble material, such as polymers may be used. Important is that the material has a water resistance to a certain degree such that the sleeve can be used for several minutes. Experiments have shown that a time of 3 minutes is typically sufficient for emptying an ostomy pouch, though many users may find it sufficient with 2 minutes. However, elderly people may require longer time for emptying, for example 4 or 5 or even up to 10 minutes. The sleeve can be produced with a water resistant time span matching the demands from the user such that it is ensured that the sleeve can withstand exposure to liquid on the inner side of the sleeve for a time sufficiently long before the material is dissolved. In this connection, the machine glazed inner side of the sleeve has proven to be an advantage, because the excretions are transported quickly through the sleeve reducing the time of exposure to excretions of the inner side of the sleeve.

In a further practical embodiment, the length of the tube is between 550 mm and 950 mm.

In an even further embodiment, the first opening has diameter of between 80 mm and 140 mm and the second opening has a diameter of between 30 and 140 mm, the diameter of the second opening being equal to or smaller than the diameter of the first opening.

SHORT DESCRIPTION OF THE DRAWINGS

Figure 2:
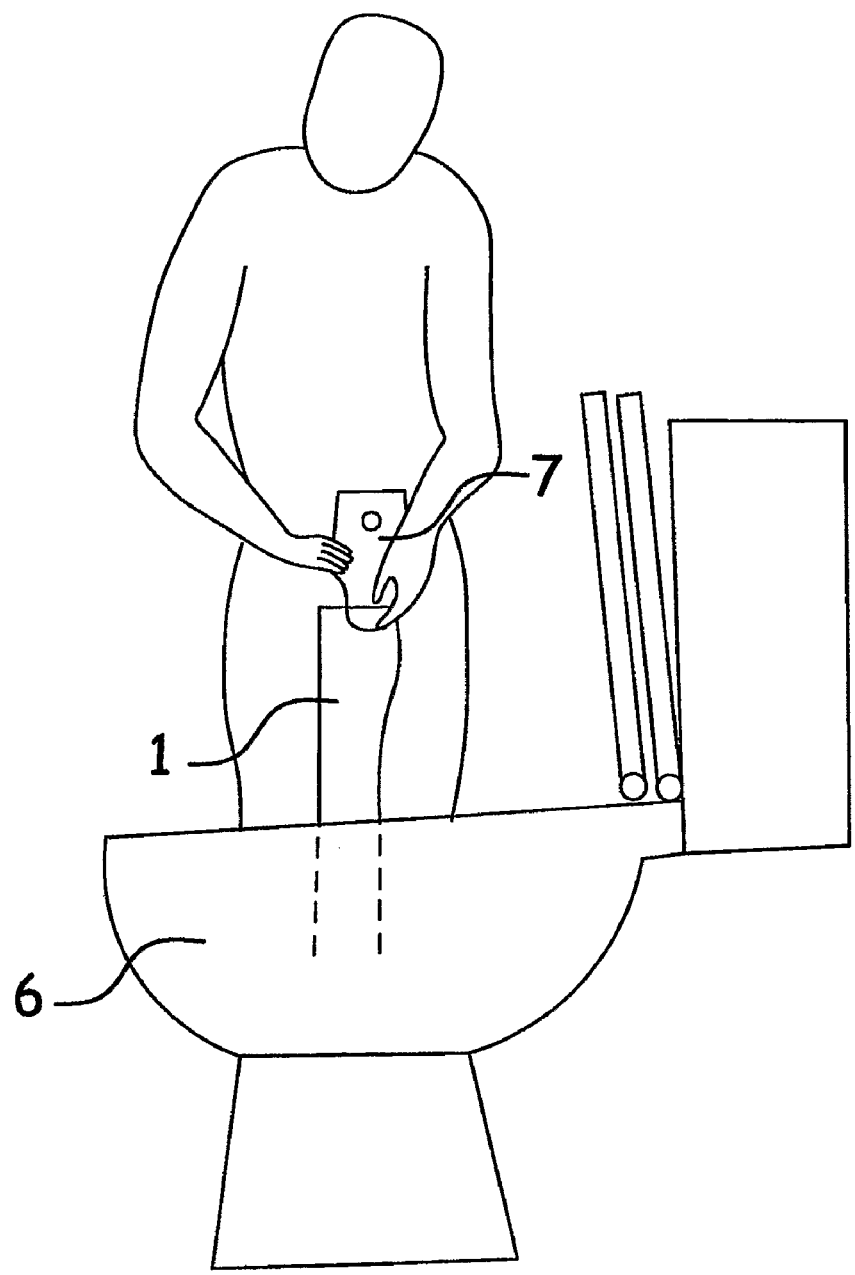
Figure 3:
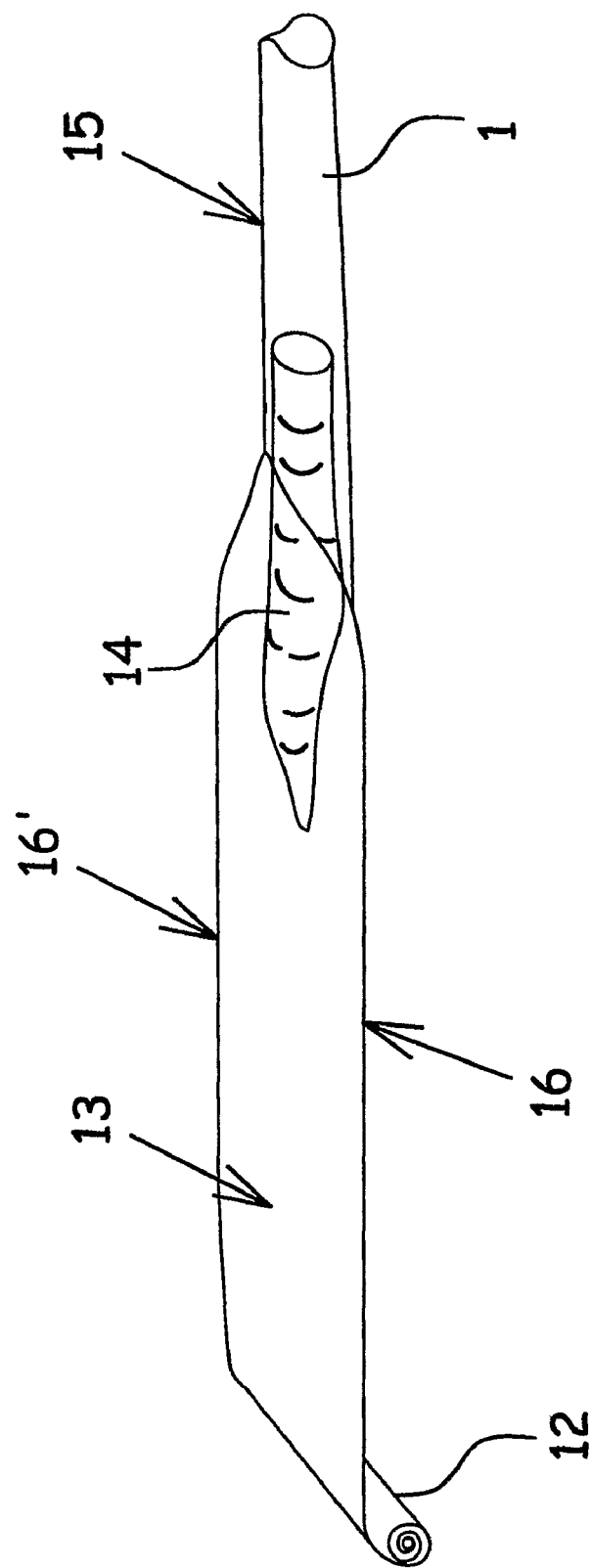
Figure 4:
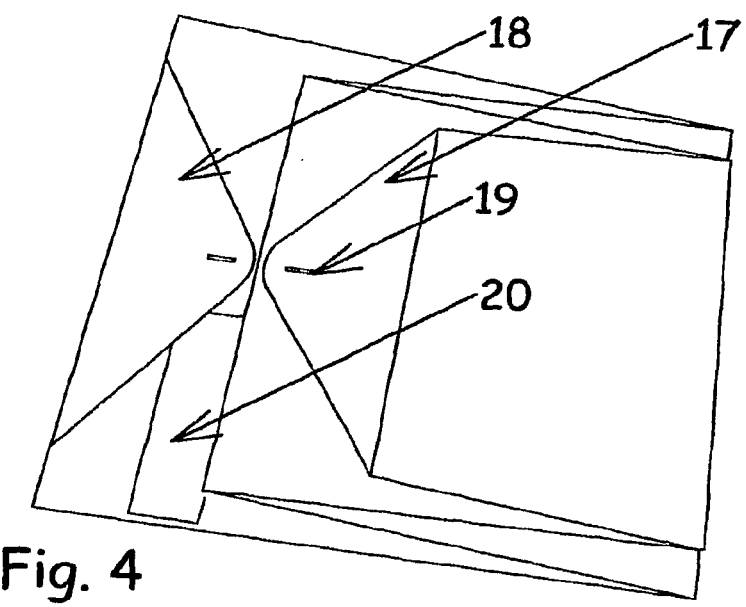
Figure 5A:
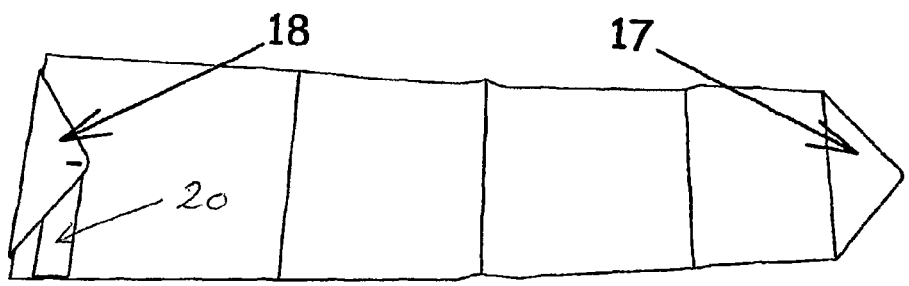
Figure 5B:
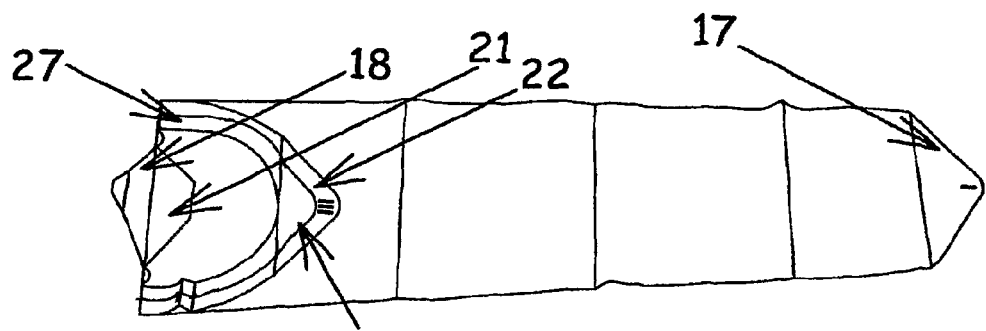
Figure 6:
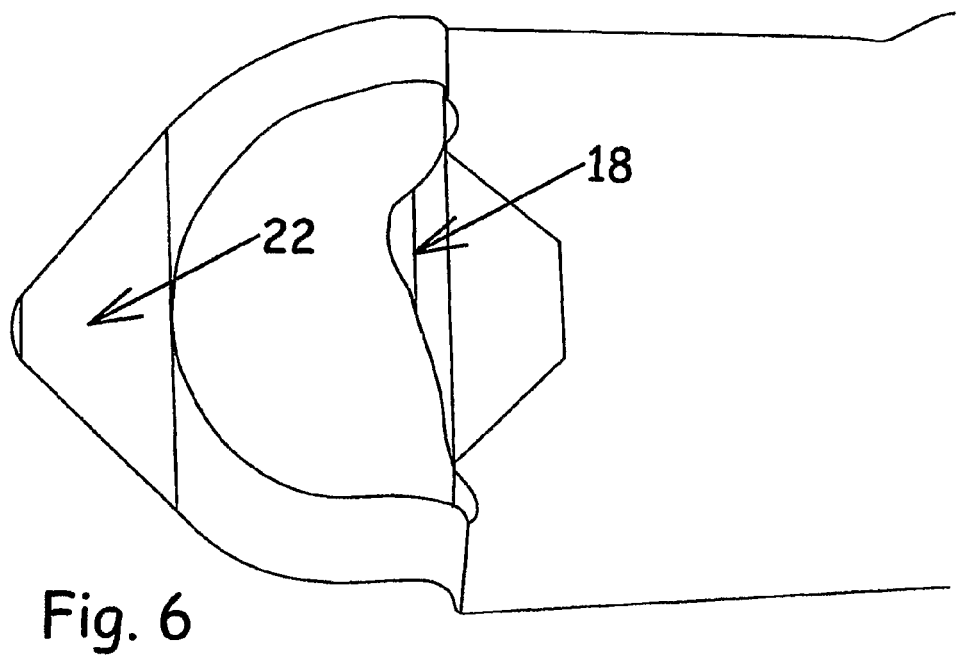
Figure 7:
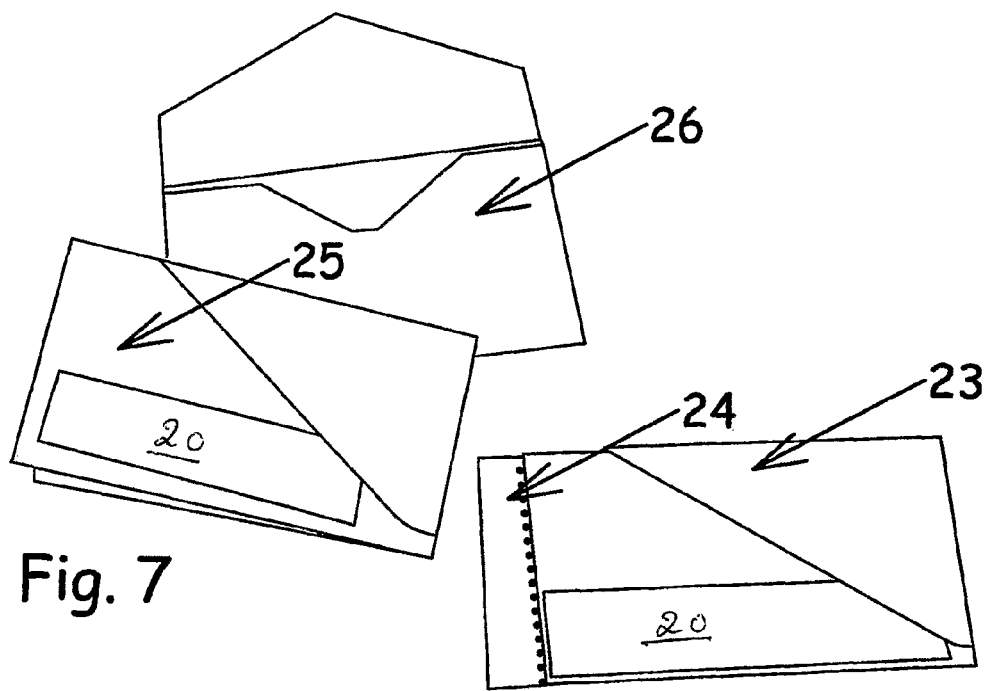

The invention will be explained in more detail with reference to the drawing, where FIG. 1 is a drawing of the sleeve according to the invention, FIG. 2 illustrates the use of the sleeve, FIG. 3 illustrates the production of the sleeve from a paper roll, FIG. 4 is a picture of a sleeve in a folded state, FIG. 5 are pictures of the a) first side and b) second side of an unfolded sleeve, FIG. 6 illustrates the handle in greater detail, FIG. 7 is a picture of a pocket size folded sleeve.

DETAILED DESCRIPTION/PREFERRED EMBODIMENT

FIG. 1 is a drawing of the sleeve according to the invention. The sleeve 1 has a tubular shape and a first end 2 with a first opening 3 for receiving ostomy discharge material and a second, opposite end 4 with a second opening 5 for discharge of the ostomy discharge material into a discharge unit, for example a toilet 6 as illustrated in FIG. 2, after guidance through the sleeve 1. In order for the sleeve 1 to be correctly positioned for receipt of excretion from an ostomy pouch 7, the sleeve 1 may be provided with glue 8 at the upper end 2 for fastening of the sleeve 1 to the ostomy pouch 7 or the body. Alternatively or in addition, the sleeve 1 may be provided with a handle for holding the sleeve 1 in place and/or for carrying it.

As illustrated in FIG. 1, the sleeve 1 has a perforation 9 with a number of holes 10 in the sleeve material. The perforation 9 ensures that air can escape from the water semi resistant, soluble sleeve 1 such that it does not float on the water in the toilet 6 but can be flushed out of the toilet 6.

The sleeve 1 according to the invention may as an example be produced from a roll 12 of paper 13 by bending the paper 13 around a mandrel 14 with a gluing 15 of the edges 16, 16' of the paper 13 in order to form the sleeve 1. The process is illustrated in FIG. 3. The glue 11 along the sleeve 1 is also illustrated in FIG. 1. The uppermost part of the ring shown in FIG. 1 is shown enforced by reinforcement ring 27 around the upper edge of the sleeve.

The illustrated sleeves could as well be produced with a closed end, especially the embodiment with the perforations. This would give the user the possibility to carry the sleeve from the place of use and to the discharge unit, for example the toilet.

FIG. 4 is a picture of a sleeve in a folded state. Such folded sleeves have a size of about 15 cm edge length and may be purchased by customers in packages with a larger number of these folded sleeves, for example 25 sleeves in a single package. With respect to the cost of such sleeves, a calculation has shown that cost for 25 sleeves according to the invention balance the costs for a single plastic re-use sleeve according to prior art on the market. In other words, only if the prior art sleeve is used more than 25 times, the costs are more favourable for the prior art single re-use sleeve than for the package of 25 disposable sleeves. Taking into account the fact that the use of disposable sleeves are much more user friendly, the product according to the invention seems convincingly superior to the prior art sleeves.

The folded sleeve is equipped with an instruction label 20 stating that the two strips 17, 18 numbered "I" 19 should be pulled in opposite directions in order to unfold the sleeve. Once unfolded, the sleeve appears with its first side as illustrated in FIG. 5a and with the opposite side as illustrated in FIG. 5b.

The second step due to the instructions label 20 before use is the opening of the strip 18 in order to reveal the area 21 with the glue for fastening the sleeve. In addition, as illustrated in FIG. 5b and in another orientation in FIG. 6, the sleeve comprises a handle 22 denoted with "III" as an additional stabilising and handling means. FIG. 5b also shows the uppermost part of the ring to be enforced by reinforcement ring 27 around the upper edge of the sleeve. In this figure the reinforcement ring 27 is shown with lips 28 that extend up a distance along the handle 22 in order for the handle to be made as stable as possible.

FIG. 7 is a picture of a pocket size folded sleeve 23 having a format about the size of a credit card. It may be held together with a seal 24 that can be torn up for use. Alternatively and for protection and for decent appearance, the sleeve 25 may be delivered in an envelope 26. Likewise the sleeves with the larger format as illustrated in FIG. 4, the more tightly folded sleeves 23, 25 may be delivered in a box package at low price. Commercially, the price for such sleeves may be only slightly higher than for the larger format folded sleeves as illustrated in FIG. 4.

The invention claimed is:

1. Ostomy irrigation sleeve having a tubular shape and a first end with a first opening for receiving ostomy discharge material and a second, opposite end with a second opening for discharge of the ostomy discharge material into a discharge unit after guidance through the sleeve, wherein the sleeve comprises a reinforcement ring made around the upper opening of the sleeve, wherein the irrigation sleeve is made of a flexible, water semi resistant material configured to be water soluble only after a certain time of exposure to liquid, wherein the certain time is at least 3 minutes.

2. Ostomy irrigation sleeve according to claim 1, wherein the material of the irrigation sleeve is water soluble paper.

3. Ostomy irrigation sleeve according to claim 1, wherein the irrigation sleeve is provided with a perforation along the sleeve for escape of air from inside the sleeve and through the perforation.

4. Ostomy irrigation sleeve according to claim 3, wherein the perforation comprises holes in the sleeve, the holes having a diameter of less 1 mm in order to prevent discharge material to flow through the perforation.

5. Ostomy irrigation sleeve according to claim 1, wherein the material contains fibers that are oriented primarily in a longitudinal direction of the sleeve for increased strength in the longitudinal direction.

6. Ostomy irrigation sleeve according to claim 1, wherein the sleeve primarily is made of a laminate of at least two sheets of fiber material, where each of the at least two sheets contains fibers that are oriented primarily in a preferred direction, but where the at least two sheets are arranged in the laminate with different preferred fiber directions.

7. Ostomy irrigation sleeve according to claim 1, wherein the sleeve is made of paper with a weight of between 15 and 50 grams per square meter.

8. Ostomy irrigation sleeve according to claim 1, wherein the sleeve is made of paper which is machine glazed on one side.

9. Ostomy irrigation sleeve according to claim 1, wherein the sleeve is made of paper that in a dry state has longitudinal pull strength of at least 1 according to a SCAN P-67 standard.

10. Ostomy irrigation sleeve according to claim 1, wherein the sleeve is made of paper that in a dry state has longitudinal tear strength of at least 100 according to a ISO 1974 standard.

11. Ostomy irrigation sleeve according to claim 1, wherein the sleeve comprises a handle (22).

12. Ostomy irrigation sleeve having a tubular shape and a first end with a first opening for receiving ostomy discharge material and a second, opposite end with a second opening for discharge of the ostomy discharge material into a discharge unit after guidance through the sleeve, wherein the sleeve comprises a reinforcement ring made around the upper opening of the sleeve, wherein the irrigation sleeve is made of a flexible, water semi resistant material configured to be water soluble only after a certain time of exposure to liquid, wherein the certain time is at least 3 minutes wherein the sleeve comprises a handle (22) and the reinforcement ring has upper lips extending a distance up along the handle for reinforcing the handle (22).

13. Ostomy irrigation sleeve according to claim 1, wherein the sleeve is folded into a credit card size for easy transport.

14. Ostomy irrigation sleeve according to claim 1, wherein the sleeve is made of paper with a weight of about 22 grams per square meter.

15. Ostomy irrigation sleeve according to claim 1, wherein the sleeve is made of paper that in a dry state has longitudinal pull strength of about 1.6 according to a SCAN P-67 standard.

16. Ostomy irrigation sleeve according to claim 1, wherein the sleeve is made of paper that in a dry state has longitudinal tear strength of about 115 according to a ISO 1974 standard.

* * * * *